United States Patent [19]

Daikuzono

[11] Patent Number: 4,736,743

[45] Date of Patent: Apr. 12, 1988

[54] VAPORIZATION CONTACT LASER PROBE

[75] Inventor: Norio Daikuzono, Tokyo, Japan

[73] Assignee: Surgical Laser Technology, Inc., Malvern, Pa.

[21] Appl. No.: 862,460

[22] Filed: May 12, 1986

[51] Int. Cl.⁴ ................................................ A61B 17/36
[52] U.S. Cl. ................................................ 128/303.1
[58] Field of Search ............ 128/4, 6, 303.1, 395–398, 128/634; 219/121 L, 121 LE, 121 LF; 350/96.1, 96.24, 96.29–96.34

[56] References Cited

U.S. PATENT DOCUMENTS

| | | |
|---|---|---|
| 2,247,258 | 1/1941 | Shepard ................................ 128/397 |
| 3,123,066 | 3/1964 | Brumley . |
| 3,236,707 | 2/1966 | Lins . |
| 3,304,403 | 2/1967 | Harper . |
| 3,467,098 | 9/1969 | Ayres . |
| 3,528,424 | 9/1970 | Ayres . |
| 3,622,743 | 11/1971 | Muncheryan . |
| 3,821,510 | 6/1974 | Muncheryan . |
| 3,834,391 | 9/1974 | Block . |
| 3,843,865 | 10/1974 | Nath . |
| 3,865,113 | 2/1975 | Sharon et al. . |
| 3,865,114 | 2/1975 | Sharon . |
| 4,069,080 | 1/1978 | Osborne . |
| 4,126,136 | 11/1978 | Auth et al. . |
| 4,185,633 | 1/1980 | Prozorov et al. . |
| 4,233,493 | 11/1980 | Nath ..................................... 128/397 |
| 4,266,549 | 5/1981 | Kimura . |
| 4,270,845 | 6/1981 | Takizawa et al. . |
| 4,273,109 | 2/1981 | Enderby . |
| 4,273,127 | 1/1981 | Auth et al. ...................... 219/121 L |
| 4,313,431 | 2/1982 | Frank . |
| 4,388,924 | 1/1983 | Weisman et al. . |
| 4,408,602 | 10/1983 | Nakajima . |
| 4,421,382 | 12/1983 | Doi et al. . |
| 4,448,188 | 5/1984 | Loeb . |
| 4,449,528 | 5/1984 | Auth et al. . |
| 4,454,882 | 6/1984 | Takano . |
| 4,469,098 | 9/1984 | Daui . |
| 4,470,414 | 9/1984 | Imagawa et al. . |
| 4,539,987 | 9/1985 | Nath et al. . |
| 4,592,353 | 6/1986 | Daikuzono . |

FOREIGN PATENT DOCUMENTS

| | | |
|---|---|---|
| 0031073 | 7/1981 | European Pat. Off. . |
| 0069351 | 1/1983 | European Pat. Off. . |
| 0105706 | 4/1984 | European Pat. Off. . |
| 2717421 | 11/1978 | Fed. Rep. of Germany . |
| 2826383 | 12/1979 | Fed. Rep. of Germany ... 128/303.1 |
| 2303516 | 10/1976 | France .............................. 128/303.1 |
| 7808175 | 3/1978 | France . |
| 8106167 | 3/1981 | France . |
| 8118036 | 3/1983 | France . |
| 8202604 | 8/1982 | PCT Int'l Appl. . |
| 8505262 | 12/1985 | PCT Int'l Appl. .............. 128/303.1 |
| 2023004 | 12/1979 | United Kingdom . |

OTHER PUBLICATIONS

"Radiation Characteristics of a Tapered Cylindrical Optical Fiber" C. T. Chang & D. C. Auth, J. Opt. Soc. Am., vol. 68, No. 9, Sep. 1978.

"The Laser Photocoagulationg Dielectric Waveguide Scalpel", IEEE, vol. BME-28, No. 1, Jan. 1981, Doty et al.

Primary Examiner—Max F. Hindenburg
Attorney, Agent, or Firm—Jones, Day, Reavis & Pogue

[57] ABSTRACT

A medical laser probe for contact laser surgery wherein a surgical incision, for example, is made by direct and indirect laser heating of the tissue. Direct heating is achieved in the conventional manner by direct laser irradiation of the subject tissue. Indirect heating is achieved through the use of a probe tip specially coated with infrared absorbing material. This material serves to partially absorb and partially transmit the laser energy. The absorbed laser energy heats the probe tip thereby facilitating tissue vaporization when the probe is brought into contact with the tissue. The transmitted laser energy vaporizes the tissue by the conventional irradiation thereof. The tip surface is roughened prior to application of the infrared material to enhance adhesion while an optically transparent material is placed over the tip to preclude material damage or erosion during normal tip use.

8 Claims, 4 Drawing Sheets

FIG. 10
FIG. 11
FIG. 5
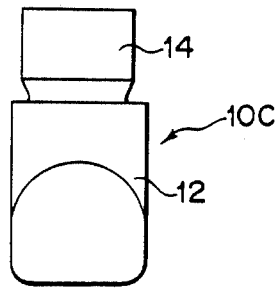
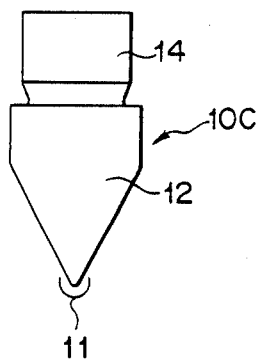
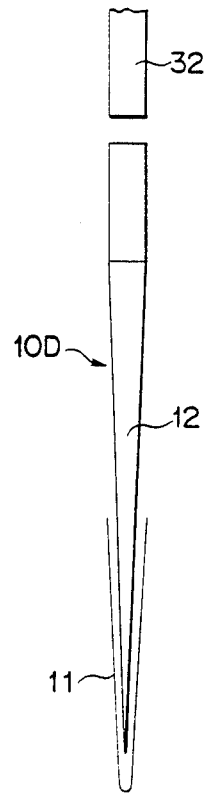
FIG. 12
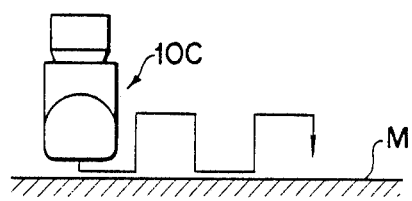

VAPORIZATION CONTACT LASER PROBE

This invention relates to a medical probe for effecting incision or vaporization with respect to tissues of human or animal organisms. More specifically, the present invention pertains to a dual mode laser surgical probe which achieves tissue vaporization by the combined heating occasioned by direct laser irradiation of the tissue as well as by heating of the laser tip which, in turn, is brought into contact with the tissue in which the incision is being made.

Laser surgery of a non-contact variety has been known for many years. In general, the simplest form of non-contact laser surgery utilizes a flexible quartz fiber for transmitting laser energy from a Nd:YAG laser source to the tissue undergoing treatment. In this system, the end of the quartz fiber serves as the probe for irradiating the tissue to effect incision or coagulation thereof. The fiber tip, however, must be maintained in spaced relationship to the tissue to avoid fouling of the fiber and, importantly, to avoid heat damage to the fiber end. Non-contact laser systems utilizing a laser transmissive member at the output end of the fiber to focus or otherwise alter the radiation characteristics of the fiber have also been proposed, for example, by Enderly, U.S. Pat. No. 4,273,109.

Such non-contact laser irradiation systems, however, exhibit poor operating efficiency as well as poor reproducibility. In general, it is necessary to maintain a fixed spacing between the output end of the laser probe or fiber and the tissue undergoing treatment in order that the laser energy density at the tissue remains constant. However, in the conventional non-contact laser irradiation system, it is difficult to keep the distance constant, especially when the surgical procedure is being performed remotely through use of an endoscope. In addition, the non-contact irradiation system exhibits a significant disadvantage in that the laser beam is backscattered from the surface of the tissue and a considerable percentage of the radiated laser energy is lost.

The inventor of the present invention has previously proposed an improved probe having a tip member which is made, for example, of an artificial sapphire disposed in front of an optical fiber through which the laser energy passes enroute the tissue undergoing treatment. In view of the properties of the tip member, in particular, its higher melting temperature, the probe can be maintained in direct contact with the tissue with a corresponding improvement in procedure efficiency and reproducibility.

This new contact laser irradiation system, however, still requires substantial output from a laser generating unit, often in excess of 40 to 50 watts for incision or vaporization, although the required output depends upon the mode of treatment. This necessitates use of a large-scale laser generating unit, including its associated bulky power supply, which is expensive and non-portable. The laser probe of the present invention produces the required tissue heating at substantially reduced laser power levels.

More specifically, the present invention relates to a laser probe in which the outside radiating surface of the probe is covered with a thin layer of infrared absorbing material such as manganese dioxide ($MnO_2$). The manganese dioxide absorbs some of the laser energy as it passes from the probe thereby heating the tip region of the probe to, for example, about 700° C. When the heated outer surface of the probe is brought into contact with the tissue, the tissue adjacent thereto is carbonized due to the heat. Thus, vaporization of the surface tissue is significantly enhanced. However, as noted, all of the laser energy is not absorbed by the infrared absorbing material and a part of the laser beam is passed directly to the tissue. This direct irradiation of the tissue enhances the vaporization of the carbonized tissue as it passes therethrough into the tissue below. Thus, the vaporization is further accelerated. The passage of the radiated laser beam through the carbonized layer advantageously performs a hemostatis effect in the tissue.

In the conventional probe, there is little vaporization of the tissue directly due to probe heat, rather, vaporization is limited by the reaction within the tissue of the laser energy as it penetrates into the tissue. In the present invention, by contrast, vaporization is not limited to heat generated by direct laser irradiation but includes the heat of the probe tip as it is brought into physical contact with the tissue. This heat, as noted, is generated by reason of the absorption of laser energy in the coated surface of the probe tip.

In this connection, it is to be noted that while an output from the laser generating unit of 40W or more is needed in the conventional probe for vaporization, 5 to 10W, or in some cases, even 1 to 5W will suffice in the probe of the present invention or effecting vaporization or incision.

The infrared absorbing material may be deposited on the smooth surface, but it is preferably deposited in concaved portions of an uneven, roughened outer surface of the probe. In the latter case, the infrared absorbing material is generally protected against being dislodged or detached and there is the further advantage that irregular laser reflections within the concaved portions of the tip serve to enhance laser interaction with the surface absorbant material thereby accelerating heat generation.

Since the fine particles of heat absorbing material may, notwithstanding the improved adherence of this material to the roughened surface, become dislodged or possibly subjected to oxidation, a protective coating of heat-resistant ceramic material is preferably placed over the heat absorbing tip end of the probe. The coating, of course, must be substantially transparent to the laser energy.

It is therefore an object of the present invention to provide a medical probe which is capable of performing tissue incision or vaporization at power levels lower than required by conventional laser probes.

BRIEF DESCRIPTION OF THE DRAWINGS

FIG. 5 is an elevation view of an alternate embodiment of the probe according to the preseent invention;

FIG. 10 is a side elevational view of the probe shown in FIG. 9;

FIG. 11 is a front elevation view of the probe of FIG. 10 as it appears apart from its mounting connector; and FIG. 12 is an explanatory view of the force-cutting for incision using the probe of FIGS. 9–11.

PREFERRED EMBODIMENT OF THE INVENTION

Figure 1:
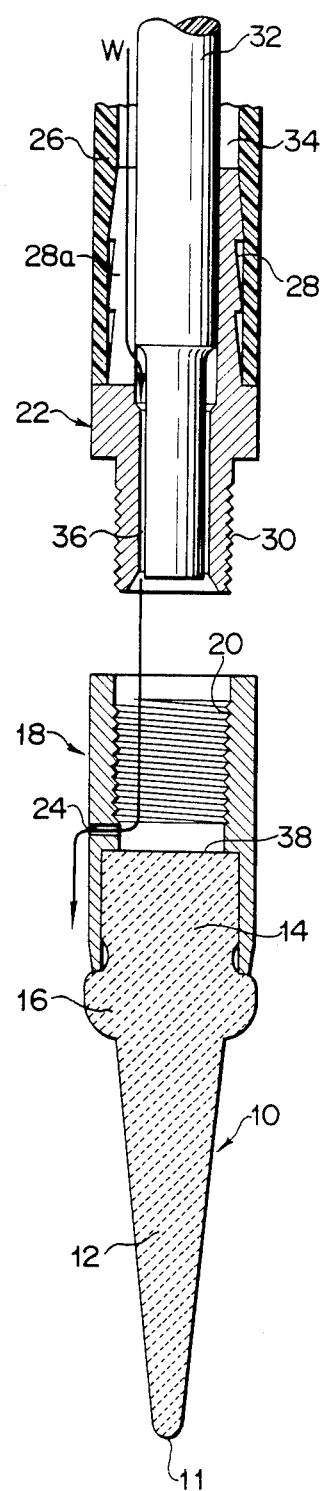
FIG. 1 is an elevation view, part in section, of the probe of the present invention and a holding member therefor.

FIG. 1 is a longitudinal sectinal view of a probe 10 according to the present invention which is mounted at the output end of a laser optical fiber 32. The fiber is connected to a source of laser energy (not shown).

Probe 10 is fabricated from a laser transmissible material such as a natural or artificial ceramic material, for example, a natural or artificial sapphire, quartz, or diamond. Polymeric materials may also be employed. In the embodiment as illustrated, the probe 10 comprises a conically tapered main body portion 12 having, at the tip end thereof, a heat generating portion 11 of semi-spherical shape and a mounting portion 14. The main body portion 12 and the mounting portion 14 are formed integrally with each other and a flange 16 is formed between the main body portion 12 and the mounting portion 14. The probe 10 is fitted in a cylindrical female connector 18 and fixed integrally thereto by caulking the mating surfaces thereof or using a ceramic type adhesive between the mating surfaces. The female connector 18 has, on the internal surface thereof, a thread 20 which is adapted to mate with complementary threads 30 of a male connector 22 on the output end of the optical fiber 32. The female connector 18 has two holes 24 through the cylindrical connector wall which facilitate the passage of cooling water W or other fluids therethrough. The two holes are circumferentially disposed at angular spaces of 180° although only one of them is shown in FIG. 1.

On the other hand, the male connector 22 is pressedly fitted into a flexible jacket 26 fabricated of, for example, Teflon (trademark). For this press fitting, the male connector 22 has stepped portions 28 at the base portion of the male connector 22 by which the male connector 22 is firmly held by the jacket 26 so as to prevent the former from being disengaged from the latter. As noted, male connector 22 is externally threaded at 30 to mate with the internal thread 20 of the female connector 18.

An optical fiber 32 for transmitting laser energy is inserted into the male connector 22. The optical fiber 32 is disposed concentrically within the jacket 26, leaving a gap 34 therebetween for supplying cooling water. Although the fiber 32 is closely fitted in the male connector 18 at a portion adjacent to the stepped portion of the male connector, the stepped portion 28 has for example two slits 28a formed circumferentially at angular spaces of 180° for letting the cooling water W pass therethrough. A passage 36 for the cooling water W is further provided between the inner face of the tip end portion of the male connector 22 and the optical fiber 32. Cooling water W is fed, according to necessity, through the gap 34 then, in turn, through slit 28a, passage 36 and discharged through the opening 24 to cool the tissue to be treated.

A laser generating unit (not shown) is optically coupled to the input end of fiber 32. A 40 watt laser is common although tissue vaporization can be effected using probes of the present invention with laser powers in the order of 10 watts or less. The laser beam from the laser generating unit is guided through the optical fiber 32 and coupled from the output end thereof to the probe 10 through the base end face 38 thereof. The laser energy is then radiated from the outer face of the probe tip or, as discussed in more detail below, absorbed by the material coating the probe tip.

Figure 2:
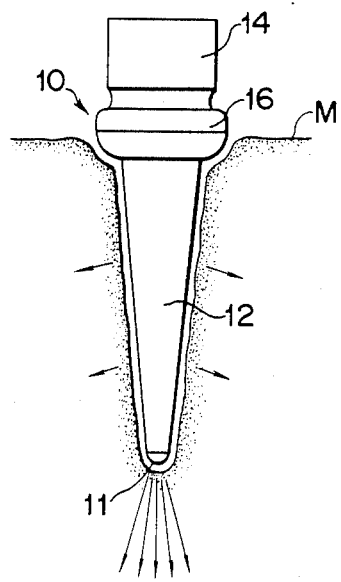
FIG. 2 is an elevation view showing the probe of FIG. 1 inserted into tissue.

FIG. 2 illustrates the dispersion and diffusion of laser energy when the probe of the present invention is employed. As the main body portion 12 of the probe 10 is formed in a conically tapered shape, some of laser energy may leak from the tapered face but the majority of the laser energy is reflected from the tapered face towards the tip end thereof. Thus, the laser beam is effectively focused and concentrated at the tip region 11 from which point the laser energy is either radiated or absorbed. Region 11 defines the heat generating portion of probe 10.

Figure 3:
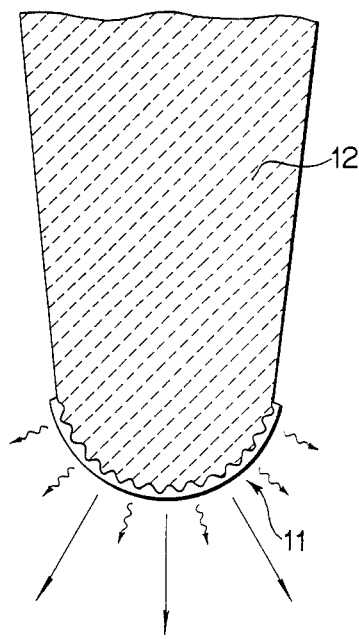
FIG. 3 is an enlarged sectional view of the probe end showing the heat generating portion thereof.
Figure 4:
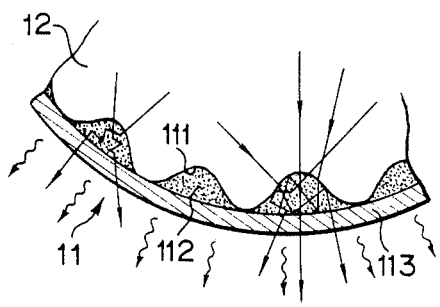
FIG. 4 is a further enlarged sectional view of the probe heat generating portion.

The outer surface of the heat generating portion 11 of the probe is frosted or roughened as shown in FIGS. 3 and 4 thereby forming an uneven and irregular contour defining apertures or recesses therein having diameter and depth of 1 to 100 $\mu$m, preferably 10 to 60 $\mu$m. The frosting or roughening process is preferably carried out by use of a computer controlled grinding wheel. More specifically, the probe undergoing surface treatment is rotated and then brought into contact with a diamond grindstone. The grindstone traces the unroughened contour of the probe, commencing from the tip of the probe, as far rearward along the conical surface as desired to define the heat generating portion 11 thereof. The computer controls, in a conventional manner, the position and speed of travel of the grindstone. In one preferred arrangement, a grindstone having particles of between 10 to 20 $\mu$m is utilized while the grindstone is moved along the probe between 3 and 6 mm/second. This results in a roughened surface contour having approximately 10 $\mu$m recesses therein. Of course, other methods may be employed to roughen the probe surface.

In the event that the depth of the recesses defining the roughened surface are too small, the amount of the infrared absorbing material held therein is correspondingly small thereby rendering the heat generating effect insufficient. Conversely, if the surface roughening is too large, excessive heat absorbing material will be retained with a corresponding decrease in the direct laser irradiation of the tissue and an increase in probe tip heating. It is preferable to roughen the tip surface within the limits set out above to maintain a proper balance between direct laser irradiation and indirect heating caused by laser absorption at the probe tip.

Referring to FIG. 4, the infrared absorbing material 112 is received and held in the concaved portions 111 formed by the frosting or roughening process. Various compositions may be used for the infrared absorbing material including $MnO_2$, $Fe_3O_4$, $CoO$, and $Cr_2O_3$. The preferred material is manganese dioxide due to its high melting point. Graphite or carbon may also be utilized although these materials may exhibit oxidation. The particle size of the infrared absorbing material is small, typically 10 $\mu$m or less. To attach the infrared absorbing material to the frosted or roughened surface of the main body portion 12 of the probe 10, the tip end portion of the main body portion 12 is dipped in a suspension of the infrared absorbing material. As a dispersion medium, there can be suitably used water or alcohol due to their rapid drying rate. The density of the infrared absorbing material may be selected by controlling the concentration of the dispersion and/or the temperature of the dispersion for obtaining desired heat generation level. When homogeneous dispersion can not be obtained, or a surface active agent is added to the dispersion.

Alternatively, cotton impregnated with the infrared absorbing material, or preferably a dispersion of the infrared absorbing material, may be used to transfer the infrared absorbing material to the frosted or roughened surface of the probe. More specifically, ½ cc of powder is mixed in approximately 1 cc of water. Dry cotton is dipped into the powder suspension so that the cotton can absorb the powder evenly. Excess water is squeezed from the cotton before the impregnated cotton is pressed and rubbed onto the roughened tip surface. A clean piece of cotton is used to softly rub the probe tip region to remove excess powder thereon.

The infrared absorbing material 112 deposited in the concaved portions 111 of the frosted or roughened surface is preferably covered by a coating 113 to prevent damage to the absorbing material during normal use.

Although the material of the coating 113 is not critical so long as it exhibits transmissivity to laser energy as well as suitable heat resistance; an amorphous non-alkali glass or a ceramic such as silica, polyalumina, is preferably utilized. The compound $ZiO_2SiO_2$ has been found to be quite satisfactory and is mixed with isopropyl alcohol to form a solution (20% $ZiO_2SiO_2$) therewith. The protective overcoat solution may be applied in substantially the same manner as that described for the absorbing powder. Cotton is dipped into the solution and lightly painted over the powdered tip area. The probe is permitted to dry at room temperature for approximately 30 minutes, then, baked at 150° C. for another 30 minutes. The above described overcoating steps are repeated until a thickness of between 1 $\mu$m and 5 $\mu$m is achieved.

FIG. 4 illustrates the action of the roughened, impregnated tip on an incident laser beam as the beam attempts to pass through the tip region. As the laser beam enters the heat generating portion 11, the laser energy is irregularly reflected from both the randomly spaced infrared absorbing particles 112 and the surface of the concave portions 111 of the probe tip. The laser energy is partially attenuated by the heat absorbing material with the remainder ultimately being radiated from the tip. This laser energy irradiates and penetrates the adjacent tissue in the conventional manner. That portion of the laser energy absorbed is converted to heat which, in turn, raises the temperature of the heat generating tip portion 11. Although the precise temperature of this tip region depends upon the density of the infrared absorbing material adhering to the surface of the heat generating portion and the laser power, temperatures between about 500° and 700° C. are typical for probes prepared as set forth herein. It will be appreciated that such elevated probe tip temperatures substantially accelerate the vaporization of the tissue contacted by the probe.

Figure 6:
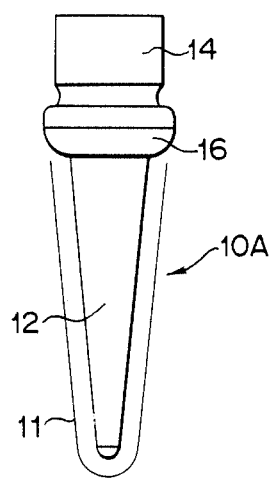
FIG. 6 is an elevation view of another alternative embodiment of the probe according to the present invention.
Figure 7:
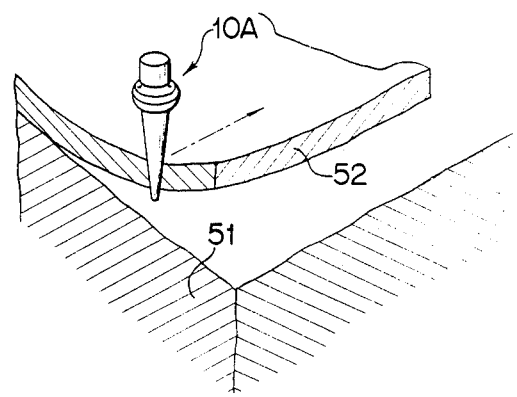
FIG. 7 is a perspective view showing an incision of the retina using the probe of FIG. 6.

Although the heat generating portion 11 is shown only at the semispherical portion of the tip end of the main body 12 in the foregoing embodiment, it may be provided at other parts of the tapered portion or along its entire length as shown at 11 in FIG. 6. In this case, the tapered portion is also frosted or roughened so that the percentage of the laser beam reaching the probe tip is reduced while the percentage of overall probe laser radiation is increased. The modified probe 10A of FIG. 6 is suitably used, for example, for selectively effecting incision of retina 52 (FIG. 7) without making incision of choroidea 51 due to the vaporization effect of heat generation at the tapered portion when the retina 52 is detached from the choroidea 51 of the eyeground.

Figure 8:
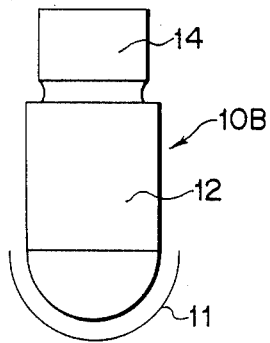
FIG. 8 is an elevation view of a yet another alternative embodiment of the probe of the present invention.
Figure 9:
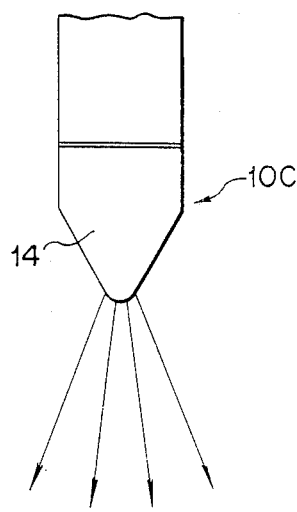
FIG. 9 is a front elevation view of another embodiment of the probe of the according to the present invention shown installed in the probe connector.

The probe may alternatively have a round shape as shown in FIG. 8. Probe 10B has a semispherical end provided with the heat absorbing material, as discussed above, at 11. This probe is suitably imployed for vaporization and incision of, for example, a constricted part of an esophagus.

The configuration of the probe may alternatively be such that the opposite sides of the tip end of a cylinder are bevelled thereby defining a wedge-shaped end as shown in FIGS. 9 to 12. This type of probe 10C may be used in such a manner that it is strongly pressed against the tissue M to make force-cutting for effecting the incision of the tissue M.

The length of the heat generating portion 11 of the probe 10 as illustrated in FIGS. 1 to 10 may be suitably determined according to the injection depth of the probe into the tissue M and it may in general be within a range of from 1.0 to 7.0 mm. Although the tip end of the heat generating portion 11 is not always required to be in semispherical shape, a pointed end of the heat generating portion would possibly be broken and therefore the tip end of the heat generating portion is preferably be rounded. The flange 16 as described before functions as an abutment or stop for positioning of the probe 10 in the tissue M when the probe 10 is injected into the tissue M until the forward end face of the projected flange 16 abuts against the tissue M. However, the flange 16 may of course be omitted.

FIG. 13 illustrates a further form of the probe in which the heat generating portion 11 is extended to the intermediate portion of the taper. This type of probe 10D may be fitted to a surgical contact scalpel.

I claim:

1. A medical laser probe for conveying laser energy from the output end of an optical laser waveguide to a tissue undergoing laser treatment, the probe comprising laser transmissive material having a laser energy input region for receiving laser energy from an optical waveguide and a laser energy radiation surface, the radiation surface defining a generally non-planar contour, the laser energy from the input region being propagated through the probe transmissive material to be incident on the probe radiation surface; infrared absorbing means formed on and conforming with the contoured radiation surface for converting a predetermined percentage of the laser energy incident thereon into heat energy, whereby said heat energy increases the temperature of the radiation surface thereby enhancing vaporization of tissue in contact therewith and the laser energy not converted into heat energy by the infrared absorbing means irradiates the tissue adjacent the radiation surface.

2. The medical laser probe of claim 1 wherein the infrared absorbing means is covered by a coating of a laser transmissive material.

3. The medical laser probe of claim 2 wherein the coating is made of amorphous non-alkali glass.

4. The medical laser probe of claim 2 wherein the coating is $ZiO_2SiO_2$.

5. The medical laser probe of claim 1 wherein the probe radiating surface is irregular and uneven whereby laser energy incident thereon is irregularly refracted and reflected and whereby infrared absorbing means may be received in the concaved recesses defined by said uneven surface.

6. The medical laser probe of claim 5 wherein the concaved recesses defining the uneven surface recesses range between 1 and 100 microns.

7. The medical laser probe of claim 1 wherein said infrared absorbing means is a composition selected from a group consisting of graphite, carbon, clay and titanium oxide, magnesium oxide, silicon dioxide and iron oxide.

8. The medical laser probe of claim 1 wherein the infrared absorbing means is a powder material having granule sizes less than about 10 microns.

* * * * *